United States Patent [19]
Badger et al.

[11] Patent Number: 5,891,403
[45] Date of Patent: Apr. 6, 1999

[54] APPARATUS AND METHOD FOR DISPOSAL OF EXPANDED POLYSTYRENE WASTE

[76] Inventors: Berkley C. Badger, 324 Westgate Rd., Tarpon Springs, Fla. 34689; Kevin E. Hissem, 1333 Burnnell Pkwy., Lakeland, Fla. 33805

[21] Appl. No.: 896,174

[22] Filed: Jul. 17, 1997

[51] Int. Cl.$^6$ ..................................................... A61L 2/18
[52] U.S. Cl. ........................ 422/300; 422/255; 422/261; 422/292; 422/904; 241/DIG. 38; 521/47; 524/577
[58] Field of Search ................................. 422/255, 261, 422/292, 300, 301, 901; 241/DIG. 38; 521/47; 524/577

[56] References Cited

U.S. PATENT DOCUMENTS

| | | | |
|---|---|---|---|
| 5,003,892 | 4/1991 | Bricken | 422/1 |
| 5,124,126 | 6/1992 | Ripp | 422/300 |
| 5,207,994 | 5/1993 | Suzuki et al. | 422/307 |
| 5,279,465 | 1/1994 | Stroppiana | 241/29 |
| 5,350,562 | 9/1994 | Anthony | 422/1 |
| 5,411,714 | 5/1995 | Wu et al. | 422/232 |
| 5,540,244 | 7/1996 | Brooks et al. | 134/56 R |
| 5,674,914 | 10/1997 | Abe et al. | 422/901 |

*Primary Examiner*—William H. Beisner
*Assistant Examiner*—Fariborz Moazzam
*Attorney, Agent, or Firm*—Terrance L. Siemens

[57] ABSTRACT

The present invention features a portable waste disposal unit designed to receive expanded polystyrene or similar polymeric waste. Waste is loaded into a waste reception chamber via a loading door. Once the loading door is closed and locked, a mechanical ram forces the waste charge downward into a removable tank containing a layer of a solvent such as perchloroethylene and an upper layer of water. The waste is dissolved in the solvent and stored until the tank is either removed or drained and the contents shipped to an appropriate waste recovery facility. The small size of the portable waste disposal unit makes it ideal for location near the source of the waste to be recycled. Significant compacting of wastes such as expanded polystyrene may be realized by dissolving the waste in a solvent such as perchloroethylene. In addition, the first step of a recycling process is effectively accomplished within the inventive unit.

16 Claims, 2 Drawing Sheets

APPARATUS AND METHOD FOR DISPOSAL OF EXPANDED POLYSTYRENE WASTE

This application is related to the application, Ser. No. 08/818,953 filed Mar. 14, 1997, now abandoned, which is incorporated herein by reference.

FIELD OF THE INVENTION

The present invention relates to a portable polymer/elastomer waste disposal unit and, more particularly to a waste disposal unit for the liquification by dissolution of expanded polystyrene whereby the volume of waste is greatly reduced and the first step of an effective recycling process takes place in situ.

BACKGROUND OF THE INVENTION

Synthetic polymeric and elastomeric resins are widely utilized for fabricating packaging and packing products. A typical example is expanded polystyrene cups, plates, and the like used in the fast food industry. Generally, objects made from these materials are discarded after a single use. If these products are merely placed in landfills, they are lost for subsequent recovery of the constituent material. Furthermore, disposal in landfills is objectionable since such products, as is typical with synthetic resins generally, are of low density and occupy an inordinate volume within the landfill. This, coupled with the fact that many of these materials take very long periods of time to break down in a landfill, make a strong case for recycling such products.

DISCUSSION OF THE PRIOR ART

Many attempts have been made heretofore to effectively recycle such products. Such recovery or separation of plastics from waste has relied upon many methods. For example, the recycling of plastic films is taught in U.S. Pat. No. 5,540,244; issued to J. Douglas Brooks et al. on Jul. 30, 1996. In this process, the film is washed in aqueous solution and dewatered by pressure.

Plastics, together with other materials, are heated and separated by passing the mixture through a sieve in a process described in U.S. Pat. No. 5,350,562, issued to Frank H. Anthony on Sep. 27, 1994.

A plastics recovery process shown in U.S. Pat. No. 5,411,714, issued to Arthur C. Wu et al. on May 2, 1995, produces outputs of solid, liquid, and gaseous phases.

A process utilizing a diffusion material which combined with plastics being treated is described in U.S. Pat. No. 5,279,465, issued to Fernando Stroppiana on Jan. 18, 1994.

None of the prior art processes utilizes dissolution of plastics in a solvent in a portable waste disposal unit. None of the above inventions and patents, taken either singly or in combination, is seen to describe or suggest the instant invention.

SUMMARY OF THE INVENTION

The present invention features a portable waste disposal unit designed particularly to receive expanded polystyrene waste. Waste is loaded into a waste reception chamber via a loading door. Once the loading door is closed, a mechanical ram forces the waste charge downward into a removable tank containing a lower layer of a solvent such as perchloroethylene and an upper layer of water. The waste is dissolved in the solvent and stored until the tank is either removed or drained and the contents shipped to an appropriate waste recovery facility.

BRIEF DESCRIPTION OF THE DRAWINGS

A complete understanding of the present invention may be obtained by reference to the accompanying drawings, when taken in conjunction with the detail description thereof and in which.

DESCRIPTION OF THE PREFERRED EMBODIMENT

Generally speaking this invention relates to a portable polymer/elastomer waste disposal unit and, more particularly to a waste disposal unit for the liquification by dissolution of expanded polystyrene, whereby the volume of waste is greatly reduced and the first step of an effective recycling process takes place in situ.

Figure 1:
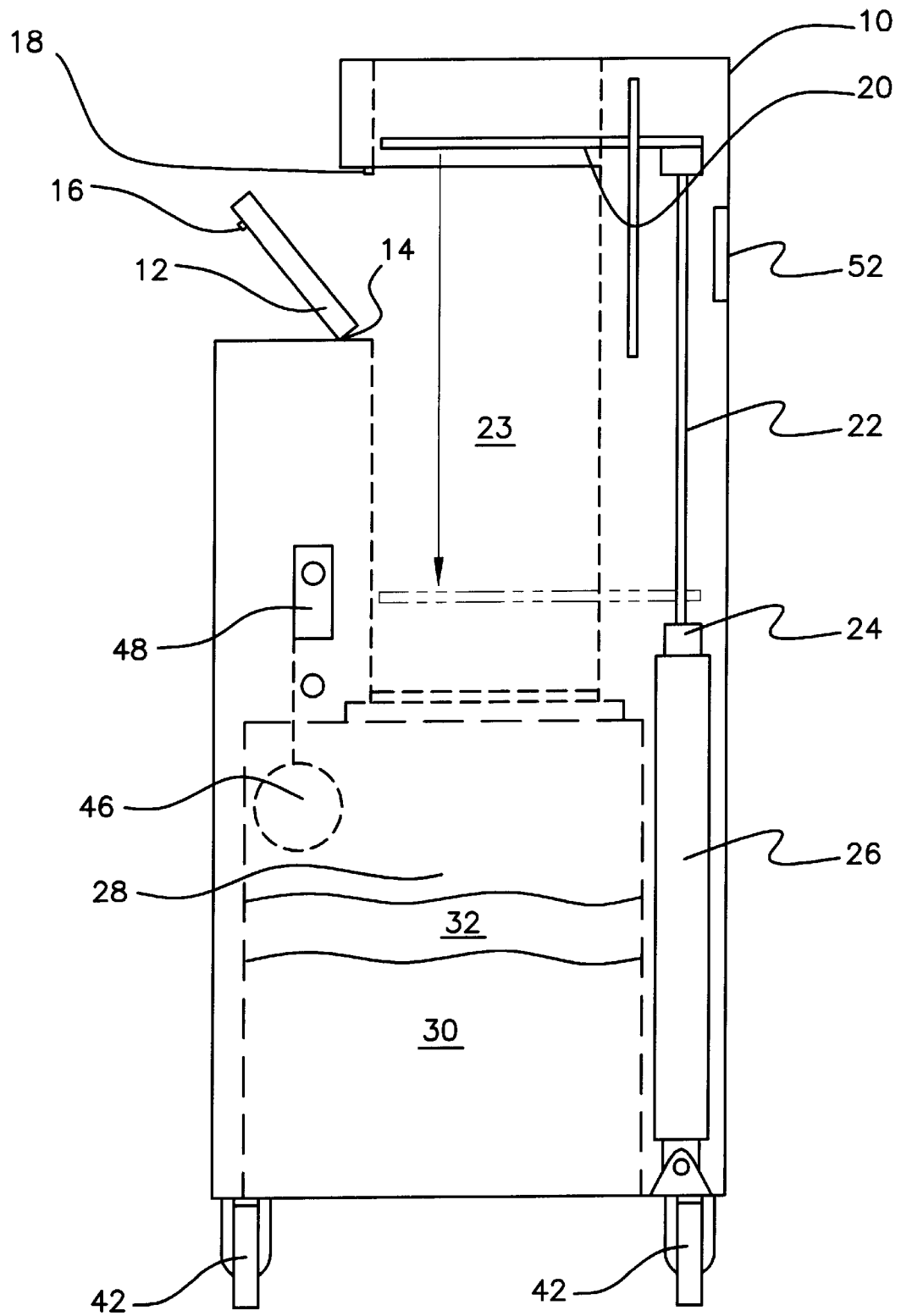
FIG. 1 is a side, schematic view of the portable waste disposal unit.

Referring first to FIG. 1, there is shown a side schematic view of the portable waste disposal unit. A chassis 10 serves as a support and housing for the various components of the portable waste disposal unit. Door 12 is affixed to chassis 10 by spring-loaded hinge 14. Hinge 14 tends to keep door 12 in a closed, sealed position unless held open, as is depicted, by an operator (not shown) grasping and pulling handle 16. A locking mechanism 18 is attached to chassis 10 so as to engage the upper region of door 12 when door 12 is in a closed position. In the preferred embodiment, locking mechanism 18 is a mechanical latch. The required locking function could easily be accomplished by an electro-mechanical, pneumatic, or hydraulic mechanism as well as by the mechanical device chosen for purposes of disclosure. A compacting plate or piston 20 is normally positioned near the top of chassis 10 just above the top of door 12. Compacting plate 20 defines the top of a waste reception chamber 23. Plate 20 is attached to an end of rod 22 which is located at the rear of chassis 10. Rod 22 is attached to plunger 24 which forms part of pneumatic cylinder 26. The lower end of pneumatic cylinder 26 is anchored to the bottom of chassis 10. Pneumatic cylinder 26 is generally a bi-directional cyclinder i.e., a pneumatic cyclider designed to move its internal piston (not shown) in either of two directions depending upon the selective application of compressed air. This bi-directional movment allows rod 22 to selectively be moved up or down. A removable tank 28 is adapted to hold a layer of an appropriate solvent 30. In the preferred embodiment, the solvent 30 is perchloroethylene but it will be obvious to those of skill in the art that choice of solvent depends upon the type of polymeric waste being disposed of and upon other operating and/or environmental requirements. An important consideration in the choice of solvent 30 is the specific gravity of the solvent. A solvent having a specific gravity significantly greater than 1 (the specific gravity of water) is required for the inventive waste disposal to operate properly. A layer of water 32 is, placed in tank 28 over the layer of solvent 30. The differences in the specific gravities insures that distinct layers of solvent 30 and water 32 will be formed and maintained. Water layer 32 tends to prevent evaporation of solvent 30 and thereby minimizes the escape of fumes from solvent 30.

Figure 2:
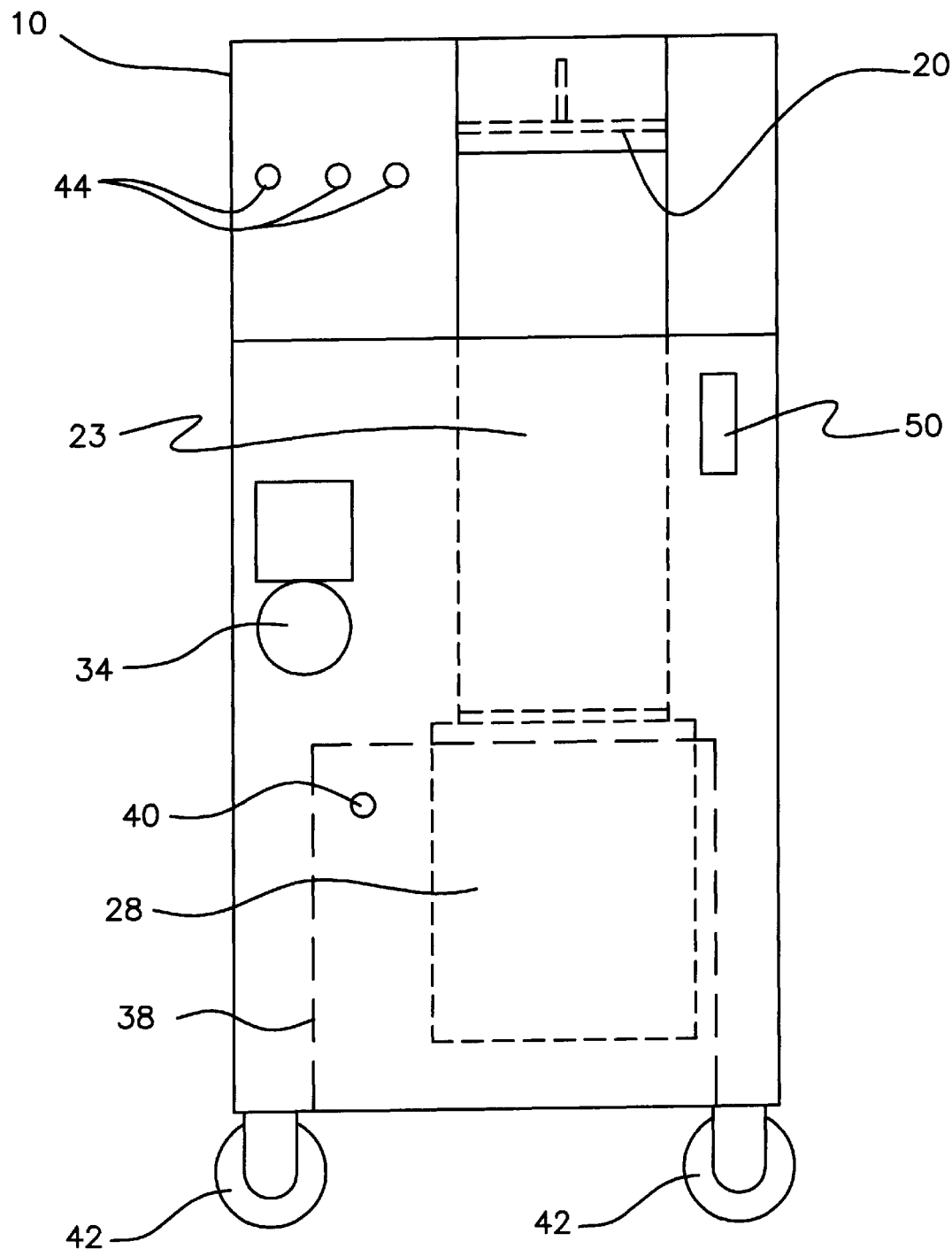
FIG. 2 is a front, schematic view of the portable waste disposal unit.

Referring now also to FIG. 2, there is shown a front, schematic view of the inventive portable waste disposal unit. An air compressor 34 is located above tank 28 near the front of chassis 10. Compressor 34 is connected to pneumatic cylinder 26 by means of tubing (not shown). An electromagnetic control valve (not shown) may be used to control the flow of compressed air to pneumatic cylinder 26. In the preferred embodiment, the operation of air compressor 34 is used to control actuation of pneumatic cylinder 26. Both the valve (if present) and air compressor 34 may be controlled by one or more simple, operator-actuated switches 44 or by a sophisticated control system (not shown) using any variety of timers, sensors, or the like to automatically or semi-automatically control the waste disposal unit. A power/logic control unit 50 contains the circuit boards, relays, pneumatic valves and any other components necessary for the control of the inventive portable waste disposal unit. An optional float-actuated switch 48, operated by float 46 in tank 28, may be used to disable operation of the waste disposal unit when the level of solvent 30 and water 32 becomes too high in tank 28. Optionally, an indicator light (not shown) could be used to notify an operator that a full tank condition exists. Compressor 34 is operated by 117 V.A.C. line current provided to the unit by a normal line cord and plug (not shown). The specific control circuits or methods are standard and numerous and varied implementations thereof will be obvious to those skilled in the art of electrical controls.

A door 38 in the front of chassis 10 allows access to removable tank 28. Door 38 is normally secured by keylock 40. Keylock 40 could easily be adapted to include an electrical interlock function to prevent the operation of the waste disposal unit while door 38 is open or unlocked. In the preferred embodiment of the waste disposal unit, tank 28 is designed for removal. In alternated embodiments, tank 28 could be permanently installed in chassis 10 and a pumping arrangement employed to empty tank 28 and to replenish solvent 30 and water 32.

Chassis 10 may be built as a vapor-proof enclosure by the incorporation of proper seals and gaskets (not shown) on door 12 and door 38. A vent 52 in the upper rear portion of chassis 10 is provided to equalize interior and exterior pressure. Vent 52 could be equipped with an appropriate filter cartridge to eliminate any solvent fumes from leaving the interior region of chassis during the times when both door 12 and door 38 were closed. In addition, vent 52 could be configured for attachment to a power-driven ventilation system if required by particular operating circumstances.

Casters 42 at the four lower corners of chassis 10 provide mobility to the unit. In the preferred embodiment, the overall dimensions of the unit are approximately 36 inches wide, 30 inches deep and approximately 59 inches high. This compact size allows for the placement, use and storage of the unit in a wide variety of locations close to the places where the expanded polystyrene or other polymeric waste is generated.

The inventive waste disposal unit is operated by loading a charge of expanded polystyrene (not shown) to be recycled into waste-reception chamber 23 via door 12. After chamber 23 is filled to capacity or all of the available expanded polystyrene has been loaded, door 12 is closed and secured by locking mechanism 18. The waste charge will be floating on top of water layer 32 in tank 28 due to the expanded polystyrene being lighter than water. The appropriate operator switch 44 is actuated causing air compressor 34 to be turned on. Air from compressor 34 is fed to pneumatic cylinder 26 causing rod 22 and compacting plate 20 to start moving from its rest position near the top of chassis downward in chamber 23 towards tank 28. As compacting plate 20 moves downward, the charge of expanded polystyrene is both compacted and forced downward through water layer 32 and into solvent layer 30 within tank 28. After compacting plate 20 has reached its maximum downward excursion, essentially all the charge of expanded polystyrene will have been forced from chamber 23, through water layer 32 and into solvent 32. Here, in solvent 32 the expanded polystyrene charge is dissolved, the "chemical compaction" thereby being completed. The travel of rod 22 in pneumatic cylinder 26 is next reversed and compacting plate 20 is eventually returned to its rest position near the top of chassis 10, thereby completing a cycle. Locking mechanism 18 is released allowing door 12 to once again be opened so that a new charge of expanded polystyrene may be loaded into the waste disposal unit. Once solvent 30 becomes saturated and can not dissolve any additional waste, or, if the optional level sensing switch 48 and float arrangement 46 have been implemented, tank 30 is removed by service personnel and a new tank having appropriate levels of water 32 and solvent 30 is placed in the waste disposal unit.

Since other modifications and changes varied to fit a particular operating requirements and environment will be apparent to those skilled in the art, the invention is not considered limited to the example chosen for purposes of disclosure, and covers all changes and modifications which do not constitute a departure from the true spirit and scope of the invention.

Having thus described the invention, what is desired to be protected by Letters Patent is presented in the subsequent appended claims.

What is claimed is:

1. A portable disposal unit for buoyant polymeric waste, comprising:

a chassis;

a waste reception chamber disposed within said chassis for receiving buoyant polymeric waste;

a removable tank disposed within said chassis beneath said waste reception chamber, said tank containing a first, bottom layer of solvent, said solvent having a specific gravity greater than water, and a second, top layer of water; and a plate periodically moving substantially all said buoyant polymeric waste from said waste reception chamber through said top, water layer and into said solvent layer in said tank; whereby said polymeric waste is dissolved in said solvent.

2. The portable waste disposal unit as recited in claim 1, said waste reception chamber further comprising a first door proximate said chassis, said first door further comprising means for locking said first door in a closed, locked position during operation of said plate.

3. The portable waste disposal unit as recited in claim 2, further comprising means for moving said movable plate between a first, stored position and a second position whereby substantially all said polymeric waste is moved from said waste reception chamber, through said water layer, and into said solvent layer within said tank.

4. The portable waste disposal unit as recited in claim 3, wherein said means for moving said movable plate comprises a pneumatic cylinder.

5. The portable waste disposal unit as recited in claim 4, wherein said pneumatic cylinder is a bi-directional pneumatic cylinder.

6. The portable waste disposal unit as recited in claim 4, further comprising air compressing means operatively connected to said pneumatic cylinder and control means operatively connected to said air compressing means and to said pneumatic cylinder.

7. The portable waste disposal unit as recited in claim 6, wherein said control means comprises a switch.

8. The portable waste disposal unit as recited in claim 7, wherein said switch comprises an operator-actuated switch.

9. The portable waste disposal unit as recited in claim 7, wherein activating said switch activates said air compressing means and initiates movement of said plate from said first position to said second position.

10. The portable waste disposal unit as recited in claim 6, wherein said control means further comprises timing means for automatically returning said plate from said second position to said first position after a predetermined time.

11. The portable waste disposal unit as recited in claim 6, wherein said solvent is perchloroethylene.

12. The portable waste disposal unit as recited in claim 6, further comprising a second door operatively connected to said chassis, said second door permitting access to and removal of said tank from outside said chassis.

13. The portable waste disposal unit as recited in claim 12, wherein said second door further comprises a lock.

14. The portable waste disposal unit as recited in claim 6, wherein said chassis forms an essentially vapor-tight enclosure for said waste reception chamber and said tank and said first door and said second door further comprise sealing means disposed between said first door and said chassis and between said second door and said chassis.

15. The portable waste disposal unit as recited in claim 14, wherein said chassis further comprises venting means.

16. The portable waste disposal unit as recited in claim 6, wherein said control means further comprises manual controls adapted for operating said plate.

* * * * *